(12) United States Patent
Mosch et al.

(10) Patent No.: US 6,619,957 B1
(45) Date of Patent: Sep. 16, 2003

(54) ULTRASONIC SCALER

(75) Inventors: James G. Mosch, Sparks, MD (US); Allen G. Hoube, York, PA (US); Peter H. Werner, Columbia, PA (US); Robert F. Hecht, Baltimore, MD (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/504,129

(22) Filed: Feb. 15, 2000

Related U.S. Application Data
(60) Provisional application No. 60/120,715, filed on Feb. 16, 1999.

(51) Int. Cl.[7] .............................. A61C 1/07; A61C 1/03; A61C 1/08
(52) U.S. Cl. ...................................................... 433/119
(58) Field of Search ................................ 433/118, 119, 433/81

(56) References Cited

U.S. PATENT DOCUMENTS

| | | | |
|---|---|---|---|
| 4,378,258 A | 3/1983 | Clark et al. ................. 148/100 |
| 4,453,919 A | 6/1984 | Takeshita ..................... 433/120 |
| 5,460,593 A | * 10/1995 | Mersky et al. ................. 600/25 |
| 5,754,016 A | 5/1998 | Jovanovic et al. .......... 318/118 |
| 5,900,690 A | * 5/1999 | Gipson et al. ............... 310/316 |
| 5,993,565 A | 11/1999 | Pinkerton et al. ........... 148/104 |
| 6,106,289 A | * 8/2000 | Rainey et al. ............... 433/118 |

* cited by examiner

Primary Examiner—Nicholas D. Lucchesi
(74) Attorney, Agent, or Firm—Dale R. Lovercheck; James R. Bieber

(57) ABSTRACT

The invention provides an ultrasonic scaler, comprising: a scaler tip, actuator material, a coil, a hand-piece housing, and an air driven electrical current generator. The actuator material, the coil and the air driven electrical current generator are enclosed by the hand-piece housing. The scaler tip is connected to the actuator material. Preferably the actuator material is $[Tb_{0.30}Dy_{0.70}Fe_{1.92}]$. The invention provides an ultrasonic scaler including a scaler tip, actuator material, a coil, a hand-piece housing, and a frequency control circuit. The actuator material, the coil and the frequency control circuit are enclosed by the hand-piece housing. The scaler tip is connected to the actuator material.

19 Claims, 5 Drawing Sheets

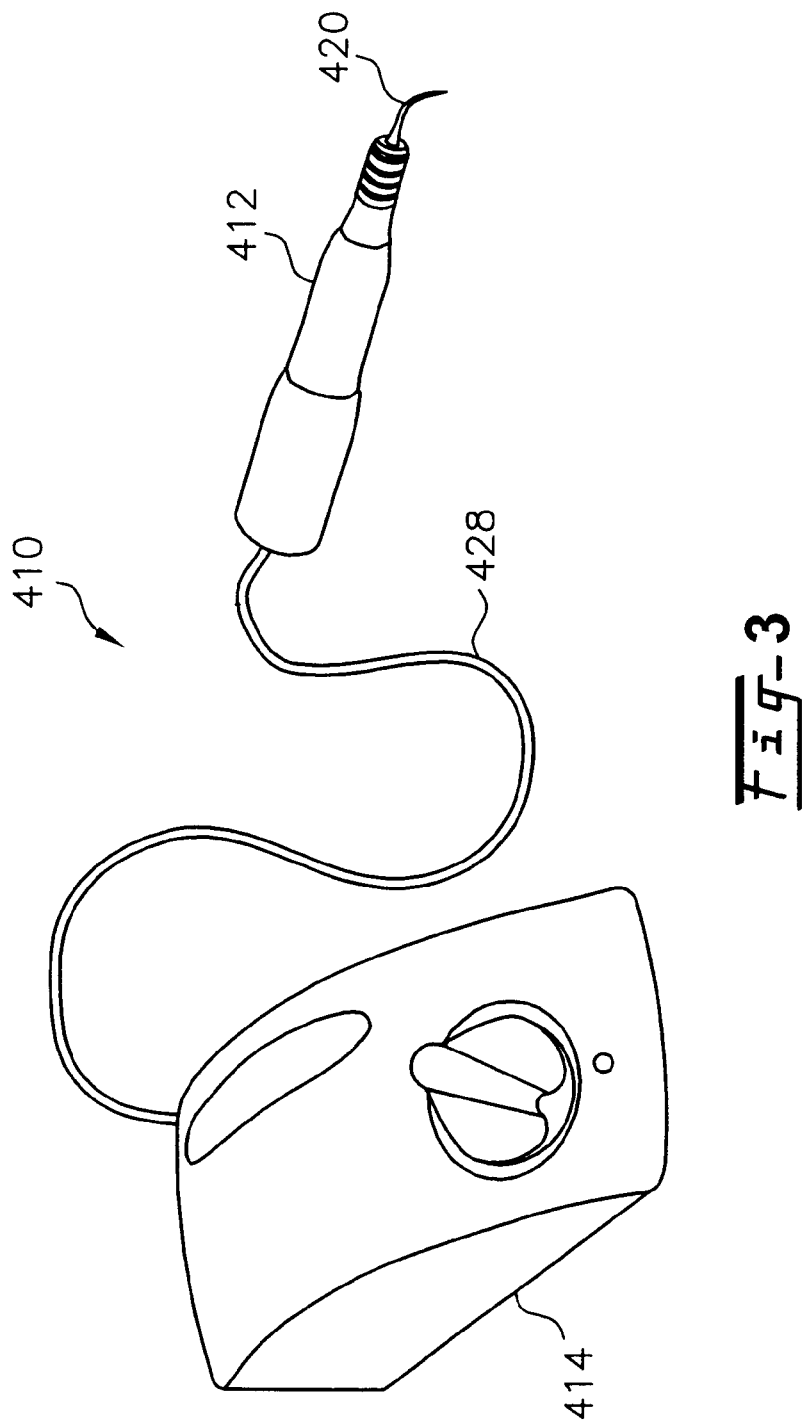

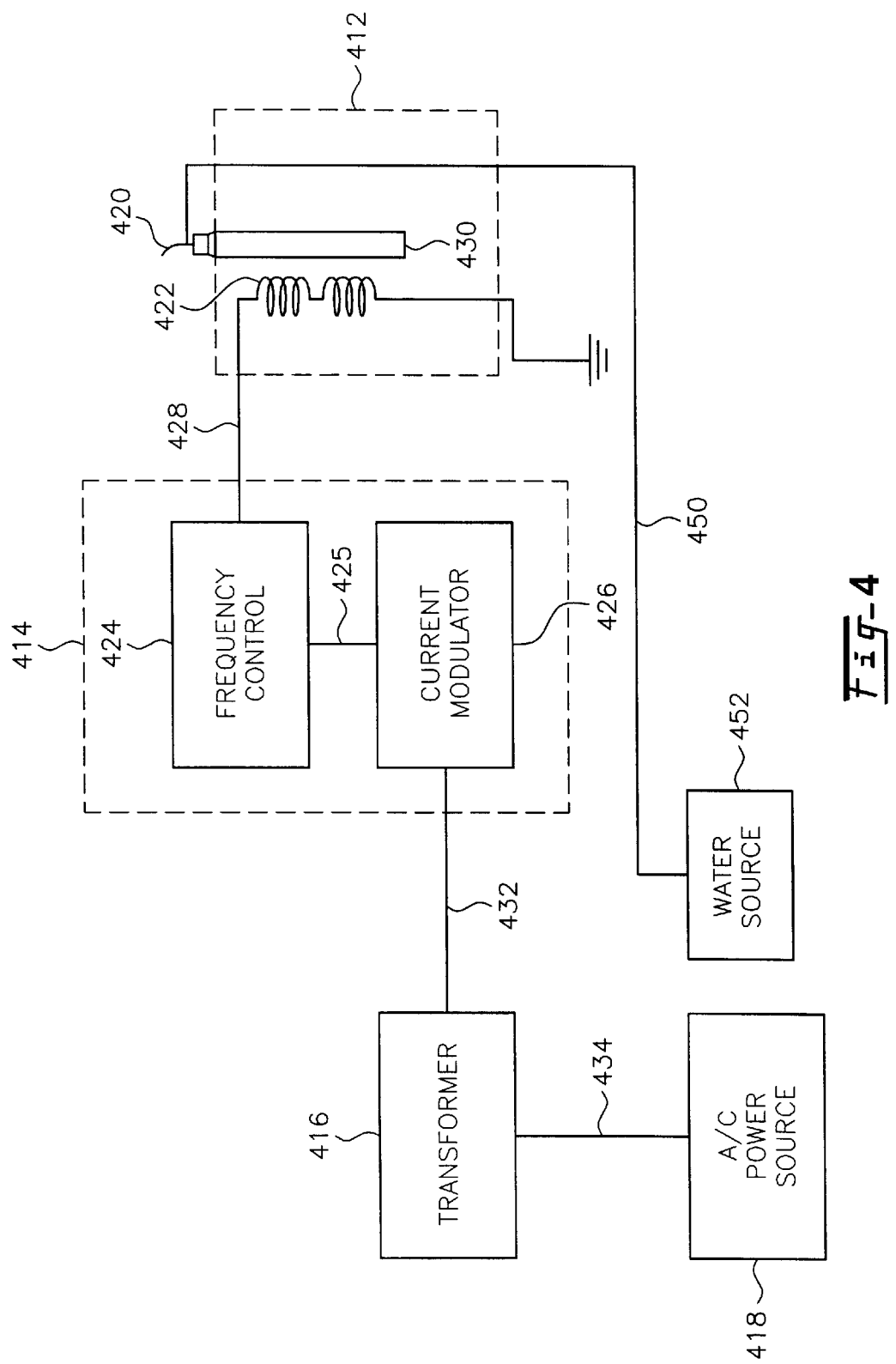

ULTRASONIC SCALER

This application claims the benefit of U.S. Provisional patent application No. 60/120,715 filed Feb. 16, 1999.

The invention relates to ultrasonic scalar hand-pieces. More specifically the invention provides ultrasonic scalar hand-pieces having a circuit to modify an electrical signals and conducting the modified electrical signals to a coil enclosed by a hand-piece housing.

BACKGROUND OF THE INVENTION

An ultrasonic scalar converts electrical energy to mechanical energy, primarily in the ultrasonic frequency range, and this mechanical energy is used to remove tooth scale. Takeshita in U.S. pat. No. 4,453,919 discloses an air driven dental scaler the disclosure of which is incorporated herein by reference in its entirety. Dentsply International Inc manufactures a Densonic TM sonic scaler which is driven by air pressure. The system operates in the ultrasonic frequency range, frequencies greater than 18K. Hertz, but is not be specifically limited to this frequency range. Operating in the ultrasonic frequency range provides beneficial scaling performance, and provides higher patient comfort in comparison to lower frequency units. The magnetostrictive actuator utilized in the system of the invention requires less power consumption than prior art systems.

Pinkerton et al disclose magnetostrictive material in U.S. Pat. No. 5,993,565 the disclosure of which is incorporated herein by reference in its entirety. Magnetostriction occurs when a material on exposure to a magnetic field develops significant strain: at room temperature, sample dimensions can change by as much as fractions of a percent. Conversely, the straining of a magnetostrictive material changes its magnetization state. Magnetostrictive materials have been used with electromagnetic actuators to form transducers which serve as, for example, ultrasonic generators or fine control valves for the metering of fluids. In these applications, variation of the magnetic field is employed to produce varying strains in the magnetostrictive material to produce a mechanical output. Conversely, a suitable magnetostrictive material might be employed as a torque or force sensor. Maximizing device performance suggests using materials having large saturation magnetostriction, .lambda..sub.s, which is a dimensionless measure of the field-induced strain frequently expressed in units of parts per million (ppm). Extremely high values of .lambda..sub.s are found in rare earth-iron compounds such as the terbium-iron compound, TbFe.sub.2, where .lambda..sub.s equals 1750 ppm for a polycrystalline sample. Unfortunately, the rare earth-iron compounds are very brittle materials having little tensile strength, an unpropitious characteristic for automotive applications requiring good mechanical properties. On the other hand, stronger and tougher materials such as steels have very limited magnetostriction: T250 maraging steel, which is currently being evaluated in torque sensors, has a .lambda..sub.s of only .about.30 ppm. The wide gulf between these two extremes offers ample opportunity and challenge for developing new magnetostrictors combining good magnetostriction with satisfactory mechanical properties. The prospect of embedding magnetostrictive powder in a strengthening matrix has been sporadically explored as follows. The Clark and Belson patent, U.S. Pat. No. 4,378,258, entitled "Conversion Between Magnetic Energy and Mechanical Energy," reported sintering cold-pressed pellets of ErFe.sub.2 with nickel and TbFe.sub.2 with iron. Few details of the properties of these materials were provided. They retain some magnetostriction, but as it turns out, the sintered bodies are brittle and of insufficient strength for many applications such as automotive sensor applications. Clark and Belson also produced resin-bonded composites of the RE-Fe.sub.2 (RE=rare earth) magnetostrictive compounds. Peters and Huston of the International Nickel Company attempted to prepare composites of SmFe.sub.2 in nickel by sintering, by extrusion and by hot pressing, but they obtained values of magnetostriction which were only modestly larger than that of the nickel alone and did not recommend the practices. See D. T. Peters and E. L. Huston, "Nickel Composite Magnetostrictive Material Research for Ultrasonic Transducer," January 1977, Naval Electronic Systems Command Contract No. N0003976-C-0017, US Department of Commerce National Technical Information Service, ADA 040336; and D. T. Peters, "Production and Evaluation of ReF(2)-Nickel Composite Magnetostrictive Materials," Final Report, January 1979, Naval Electronic Systems Command Contract No. 0003977-C-0108, US Department of Commerce National Technical Information Service, ADA 066947. Others have also made magnetostrictive composites of RE-Fe.sub.2 materials in epoxy binders.

The prior art does not disclose a hand held scaler ultrasonic, comprising a hand-piece housing, and an air driven electrical current generator, as provided by the present invention.

The prior art does not disclose a hand held scaler ultrasonic, comprising: a hand-piece housing, and a frequency control circuit, as provided by the present invention.

The problems low tip oscillation frequency of prior art hand held scalers is overcome by the present invention.

OBJECTS OF THE INVENTION

It is an object of the invention to provide an ultrasonic scaler, comprising a hand-piece housing, and an air driven electrical current generator, wherein the air driven electrical current generator is enclosed by the hand-piece housing.

It is an object of the invention to provide an ultrasonic scaler, comprising: a hand-piece housing, and a frequency control circuit, wherein the frequency control circuit is enclosed by the hand-piece housing.

BRIEF DESCRIPTION OF THE DRAWING

FIG. 3 is a perspective view of a hand-held ultrasonic scaler system having a frequency control circuit enclosed by the hand-piece housing in accordance with the invention.

FIG. 4 is a schematic view of the hand-held ultrasonic scaler system shown in FIG. 3.

SUMMARY OF THE INVENTION

The invention provides an ultrasonic scaler, comprising: a scaler tip, actuator material, a coil, a hand-piece housing, and an air driven electrical current generator, wherein the actuator material, the coil and the air driven electrical current generator are enclosed by the hand-piece housing, and the scaler tip is connected to the actuator material.

The invention provides an ultrasonic scaler including a scaler tip, actuator material, a coil, a hand-piece housing, and a frequency control circuit wherein the actuator material, the coil and the frequency control circuit are enclosed by the hand-piece housing and the scaler tip is connected to the actuator material.

DETAILED DESCRIPTION OF THE INVENTION

Figure 1:
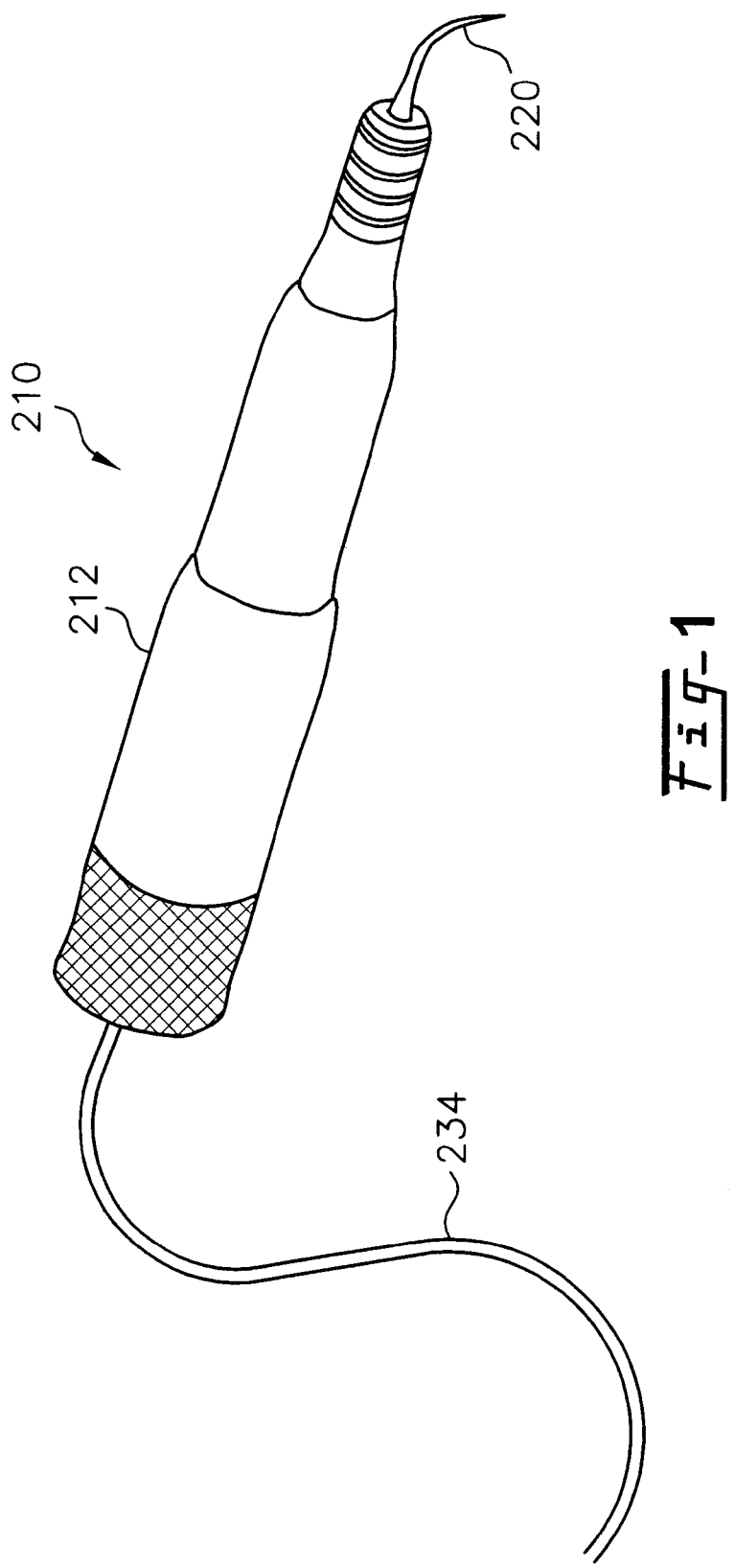
FIG. 1 is a perspective view of a hand-held ultrasonic scaler system having an air driven electrical current generator in accordance with the invention.
Figure 2:
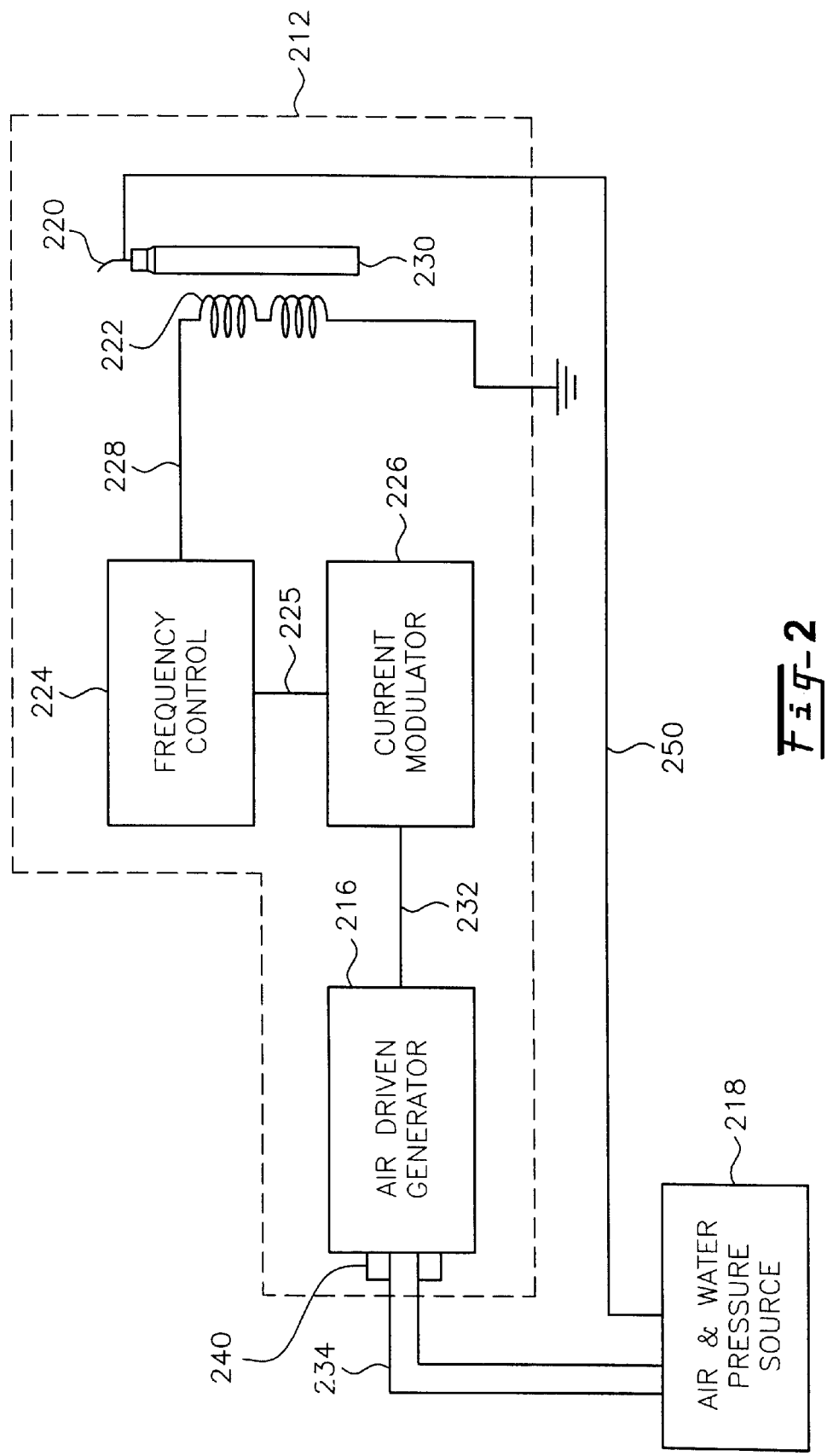
FIG. 2 is a schematic view of the hand-held ultrasonic scaler system shown in FIG. 1.

The invention is now described with more particular reference to FIGS. 1 through 4. With more particular reference to FIGS. 1, and 2 is seen a hand-held ultrasonic scaler system 210 having hand-piece housing 212. Hand-piece housing 212 encloses air driven generator 216, coils 222, frequency control circuit 224, current modulator circuit 226 and magnetostrictive material 230. A preferred magnetostrictive material for use as magnetostrictive material 230 is [$Tb_{0.30}Dy_{0.70}Dy_{0.70}Fe_{1.92}$], wherein Tb represents terbium, Dy represents dysprosium and Fe represents iron sometimes referred to as TERFENOL-D. Scaling tip 220 is connected to magnetostrictive material 230 and extends from hand-piece housing 212. Air driven generator 216 is connected to pressurized air and pressurized water source through conduit 234 and conduit connector 240. Air driven generator 216 is connected to current modulator circuit 226 through electrical conductor 232. Current modulator circuit 226 is connected to frequency control circuit 224 through electrical conductor 225. Water is conveyed through conduit 250 from pressurized air and pressurized water source 218 to tip 220.

Conduit connector 240 attaches directly to a standard high-speed dental drill cable. Air and water are supplied through the cable to drive the scalar hand-piece. For ease in user control, the hand-piece power adjustment switch will control the ultrasonic tip stroke. The scalar tip attaches to the ultrasonic motor and connecting body with a quick-disconnect feature, which will allow the tip to be easily removed without a tool. An internal water passage is provided for a lavage at the tip.

Airflow from the cable connector through the turbine of air driven generator 216 produces rotation of the turbine rotating assembly. The mechanical energy created by this rotation is converted to electrical energy in the coils of the generator. Thus, the generator produces the electrical current required to power frequency control circuit 224, current modulator circuit 226, coils 222 and magnetostrictive material 230.

The magnetostrictive material 230 converts electrical energy to high frequency mechanical energy using the magnetic field induced by an electric current in a wound wire solenoid, or coil. Thus, electrical energy input is converted into a high frequency mechanical displacement output. The mechanical energy produced is transmitted through a connecting body to the scalar tip 220. The hand-piece power adjustment switch control the power for the tip stroke. The quick disconnect feature utilizes a magnet and magnetic field to secure the tip in place.

The system 210 utilizes high-speed hand-piece drive air as a power source. The power switch located on the hand-piece provides better control of the ultrasonic tip stroke, than utilizing a foot switch air control for power variations. The hand-piece cable to scalar attachment rotates to allow the multiple tube hose to remain in its free lie position independent of the rotation of the tip. The existing high-speed water spray control on the dental unit is used to control the scalar lavage. System 210 has no electric or wire connection between hand-piece housing 212 and to air and water pressure source 218. The ultrasonic tip attaches to the unit via a quick-disconnect feature, which allows the tip to be easily removed without a tool. The entire apparatus is autoclave sterilizable. The compact size of the design allows for ease of storage.

Figure 2A:
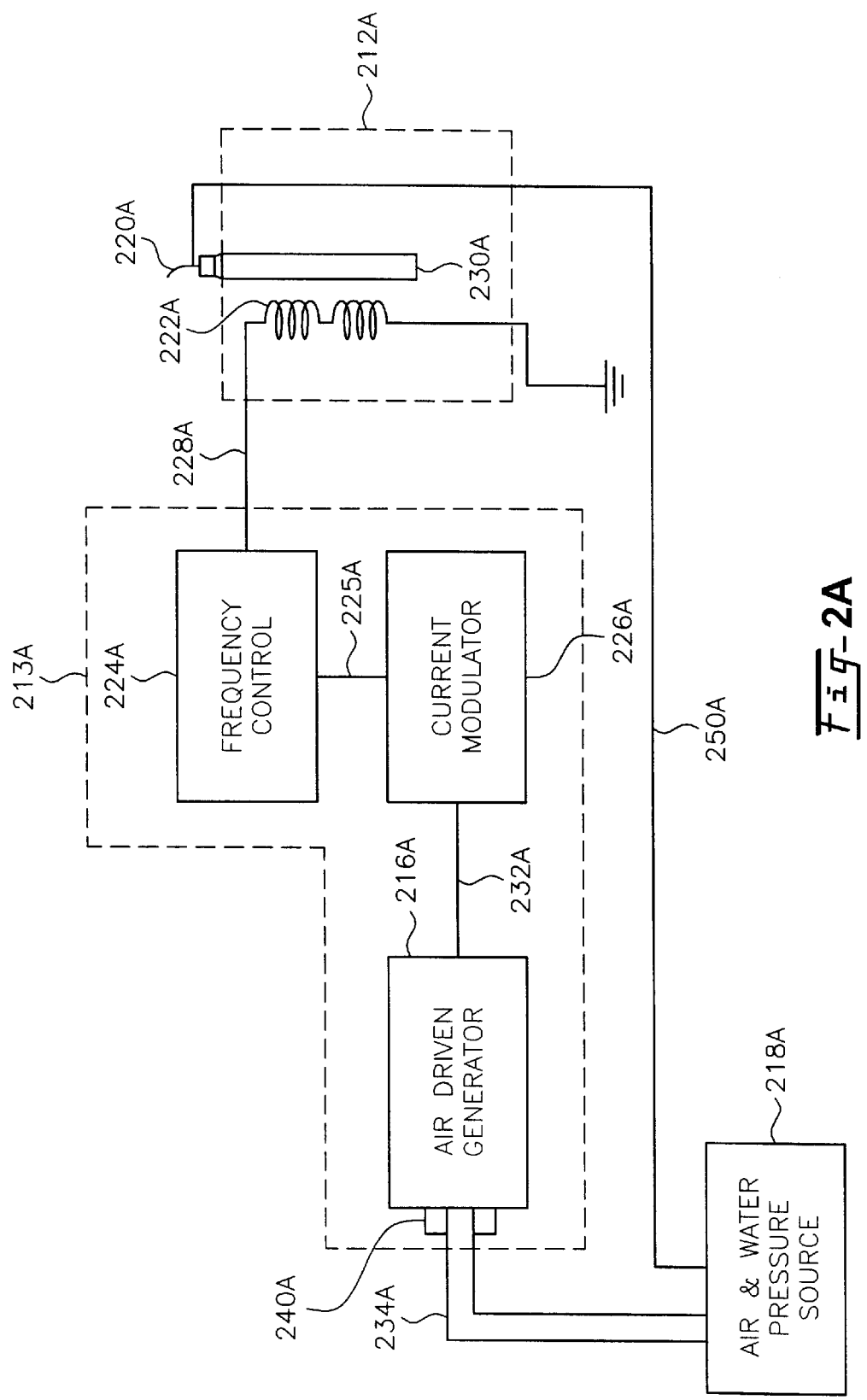
FIG. 2A is a schematic view of an alternative arrangement of components for a hand-held ultrasonic scaler system.

With more particular reference to FIG. 2A is seen a hand-held ultrasonic scaler system 210A having hand-piece housing 212A and air driven generator housing 213A. Hand-piece housing 212A encloses magnetostrictive material 230A and coils 222A. Air driven generator housing 213A encloses air driven generator 216A, frequency control circuit 224A, and current modulator circuit 226A. A preferred magnetostrictive material for use as magnetostrictive material 230A are magnetostrictive material disclosed by Pinkerton , et al in U.S. Pat. No. 5,993,565 and [$Th_{0.30}Dy_{0.70}Fe_{1.92}$], sometimes referred to as TERFENOL-D. Scaling tip 220A is connected to magnetostrictive material 230A and extends from hand-piece housing 212A. Air driven generator 216A is connected to pressurized air and pressurized water source 218A through conduit 234A and conduit connector 240A. Air driven generator 216A is connected to current modulator circuit 226A through electrical conductor 232A. Current modulator circuit 226A is connected to frequency control circuit 224A through electrical conductor 225A. Water is conveyed through conduit 250A from pressurized air and pressurized water source 218A to tip 420A.

Conduit connector 240A attaches directly to a standard high-speed dental drill cable. Air and water are supplied through the cable to drive the scalar hand-piece. For ease in user control, the hand-piece power adjustment switch will control the ultrasonic tip stroke. The scalar tip attaches to the ultrasonic motor and connecting body with a quick-disconnect feature, which will allow the tip to be easily removed without a tool. An internal water passage is provided for a lavage at the tip.

Airflow from the cable connector through the turbine of air driven generator 216A produces rotation of the turbine rotating assembly. The mechanical energy created by this rotation is converted to electrical energy in the coils of the generator. Thus, the generator produces the electrical current required to power frequency control circuit 224A, current modulator circuit 226A, coils 222A and magnetostrictive material 230A.

With more particular reference to FIGS. 3 and 4 is seen a hand-held ultrasonic scaler system 410 having hand-piece housing 412. Hand-piece housing 412 encloses coils 422, and magnetostrictive material 430. Circuit housing 414 encloses frequency control circuit 424 and current modulator circuit 426. Scaling tip 420 is connected to magnetostrictive material 430 and extends from hand-piece housing 412. Transformer 416 is connected to alternating current source 418 through conduit 434. Transformer 416 is connected to current modulator circuit 426 through electrical conductor 432. Current modulator circuit 426 is connected to frequency control circuit 424 through electrical conductor 425. Water is conveyed through conduit 450 from pressurized water source 452 to tip 420.

Circuit housing 414 corresponds to scaler housing [12] in U.S. patent application Ser. No. 09/467,494 filed Dec. 20, 1999 the disclosure of which is incorporated herein by reference in its entirety.

Frequency control circuits 224, 224A and 424 and current modulator circuits 226, 226A and 426 correspond to ultrasonic vibrator power control [114] in U.S. patent application Ser. No. 09/467,494 filed Dec. 20, 1999. Frequency control circuits 224, 224A and 424 and current modulator circuits 226, 226A and 426 are for example a system for continuous control of tip vibration disclosed by Jovanovic et al in U.S. Pat. No. 5,754,016 the disclosure of which is incorporated herein by reference in its entirety.

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. An ultrasonic scaler system, comprising:

an ultrasonic scaler having a scaler tip, actuator material, a coil, a hand-piece housing, and an air driven electrical current generator, and a pressurized air source, said actuator material, said coil and said air driven electrical current generator being enclosed by said hand-piece housing, said ultrasonic scaler being connected to said pressurized air source, said scaler tip being connected to said actuator material.

2. The ultrasonic scaler system of claim 1 wherein said actuator material is magnetostrictive material.

3. The ultrasonic scaler system of claim 1 wherein said actuator material is $[Tb_{0.30}Dy_{0.70}Fe_{1.92}]$.

4. The ultrasonic scaler system of claim 1 wherein said actuator material is a resin-bonded composite comprising a magnetostrictive compound.

5. An ultrasonic scaler system, comprising:

a scaler tip, actuator material having an output power to weight ratio greater than permanickel, a coil, a hand-piece housing, a controller housing, and a frequency control circuit, said actuator material, and said coil being enclosed by said hand-piece housing, said frequency control circuit being enclosed by said controller housing, said scaler tip being connected to said actuator material, said ultrasonic scaler system being adapted to convert electrical energy to mechanical energy, substantially in the ultrasonic frequency range, said scaler tip removing tooth scale from a tooth while said hand-piece housing is hand-held.

6. The ultrasonic scaler of claim 5 wherein said actuator material is magnetostrictive material.

7. The ultrasonic scaler of claim 5 wherein said actuator material is $[Tb_{0.30}Dy_{0.70}Fe_{1.92}]$.

8. The ultrasonic scaler of claim 5 wherein said actuator material is a resin-bonded composite comprising a magnetostrictive compound.

9. An ultrasonic scaler system, comprising:

a scaler tip, magnetostrictive material actuator material comprising terbium (Tb), and dysprosium (Dy)

a coil, a conduit, a hand-piece housing, and said actuator material, said coil, and said conduit being enclosed by said hand-piece housing, said scaler tip being actuated by said actuator material, said ultrasonic scaler system being adapted to convert electrical energy to mechanical energy, substantially in the ultrasonic frequency range, said scaler tip removing tooth scale from a tooth while said hand-piece housing is hand-held.

10. The ultrasonic scaler of claim 9 wherein said actuator material is a resin-bonded composite.

11. The ultrasonic scaler of claim 9 wherein said actuator material is $Tb_{0.30}Dy_{0.70}Fe_{1.92}$.

12. The ultrasonic scaler of claim 9 further comprising a controller housing, and a frequency control circuit, said actuator material, and said coil being enclosed by said hand-piece housing, said frequency control circuit being enclosed by said controller housing.

13. A method of using a scaler, comprising:

providing a scaler having a scaler tip, magnetostrictive actuator material comprising terbium (Tb) a coil, a conduit, a hand-piece housing, said actuator material, said coil, and said conduit being enclosed by said hand-piece housing, said scaler tip being actuated by said actuator material, said conduit being adapted to convey water from a water source to said tip said scaler being adapted to convert electrical energy to mechanical energy substantially in the ultrasonic frequency range, and removing tooth scale from a tooth with said scaler tip.

14. The method of claim 13 wherein said actuator material is a resin-bonded composite.

15. The method of claim 13 further comprising conveying water from said water source through said conduit to said tip.

16. The method of claim 13 wherein said actuator material is $Td_{0.30}Dy_{0.70}Fe_{1.92}$.

17. The method of claim 13 wherein said actuator material further comprises dysprosium (Dy).

18. An ultrasonic scaler, comprising:

a scaler tip, magnetostrictive material actuator material comprising terbium (Tb), a coil, a conduit, a hand-piece housing, and said actuator material, said coil, and said conduit being enclosed by said hand-piece housing, said scaler tip being actuated by said actuator material, said ultrasonic scaler system being adapted to convert electrical energy to mechanical energy, substantially in the ultrasonic frequency range, said scaler tip removing tooth scale from a tooth while said hand-piece housing is hand-held.

19. The scaler of claim 18 wherein said actuator material further comprises dysprosium (Dy).

* * * * *